(12) United States Patent
Hashimoto et al.

(10) Patent No.: US 10,015,436 B2
(45) Date of Patent: Jul. 3, 2018

(54) IMAGE PLAYBACK APPARATUS AND COMPUTER-READABLE RECORDING MEDIUM

(71) Applicant: OLYMPUS CORPORATION, Tokyo (JP)

(72) Inventors: Susumu Hashimoto, Hachioji (JP); Tatsuhiko Suzuki, Hino (JP); Tomoki Iwasaki, Fuchu (JP); Yuji Kutsuma, Kokubunji (JP); Toshihiro Hamada, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 68 days.

(21) Appl. No.: 15/366,062

(22) Filed: Dec. 1, 2016

(65) Prior Publication Data

US 2017/0085831 A1    Mar. 23, 2017

Related U.S. Application Data

(63) Continuation of application No. PCT/JP2015/082874, filed on Nov. 24, 2015.

(30) Foreign Application Priority Data

Nov. 27, 2014   (JP) .................................. 2014-240172

(51) Int. Cl.
  *A62B 1/04*     (2006.01)
  *H04N 5/77*     (2006.01)
  (Continued)

(52) U.S. Cl.
  CPC ......... *H04N 5/775* (2013.01); *A61B 1/00009* (2013.01); *A61B 1/00045* (2013.01);
  (Continued)

(58) Field of Classification Search
  None
  See application file for complete search history.

(56) References Cited

U.S. PATENT DOCUMENTS

| 7,659,912 B2 * | 2/2010 | Akimoto ............ A61B 1/00009 345/420 |
| 7,729,608 B2 | 6/2010 | Okubo |
| | | (Continued) |

FOREIGN PATENT DOCUMENTS

| JP | 2004-159295 A | 6/2004 |
| JP | 2006-246173 A | 9/2006 |
| | (Continued) | |

OTHER PUBLICATIONS

International Search Report dated Jan. 19, 2016 issued in PCT/JP2015/082874.

*Primary Examiner* — Hung Dang
(74) *Attorney, Agent, or Firm* — Scully, Scott, Murphy & Presser, P.C.

(57) ABSTRACT

An image playback apparatus includes: a moving image processing unit configured to generate playback-oriented moving image data from moving image data as a playback target, among moving image data recorded on a recording device; a display controller configured to play back, on a display device, the playback-oriented moving image data generated by the moving image processing unit; a release instruction input unit configured to receive input of a release signal during playback of the playback-oriented moving image data; a still image generation unit configured to generate, from the moving image data, still image data that correspond to a playback image being played back on the display device at a time of input of the release signal; and a recording controller configured to record, on the recording (Continued)

device, the still image data generated by the still image generation unit, in association with the moving image data.

8 Claims, 10 Drawing Sheets

(51) Int. Cl.
    *H04N 9/80*     (2006.01)
    *H04N 5/775*     (2006.01)
    *A61B 1/04*     (2006.01)
    *A61B 1/00*     (2006.01)
    *H04N 5/225*     (2006.01)
    *G11B 27/10*     (2006.01)
    *G11B 27/34*     (2006.01)

(52) U.S. Cl.
    CPC .............. *A61B 1/04* (2013.01); *G11B 27/105* (2013.01); *G11B 27/34* (2013.01); *H04N 5/2257* (2013.01); *H04N 5/77* (2013.01); *H04N 2005/2255* (2013.01)

(56) References Cited

U.S. PATENT DOCUMENTS

| | | | |
|---|---|---|---|
| 2005/0088540 A1 | 4/2005 | Sudo | |
| 2007/0268280 A1* | 11/2007 | Fujita | A61B 1/00045 345/204 |
| 2008/0303898 A1* | 12/2008 | Nishimura | A61B 1/0005 348/65 |
| 2009/0003732 A1* | 1/2009 | Oda | A61B 1/00045 382/305 |
| 2010/0020188 A1 | 1/2010 | Yamaguchi | |
| 2010/0182412 A1* | 7/2010 | Taniguchi | A61B 1/041 348/65 |
| 2011/0234780 A1* | 9/2011 | Ito | A61B 1/05 348/65 |
| 2012/0002026 A1* | 1/2012 | Honda | A61B 1/00009 348/65 |
| 2012/0130171 A1* | 5/2012 | Barak | A61B 1/00009 600/117 |
| 2012/0162401 A1* | 6/2012 | Melder | H04N 7/183 348/65 |
| 2013/0152020 A1* | 6/2013 | Nishiyama | A61B 1/00009 715/835 |
| 2015/0320299 A1* | 11/2015 | Krupnik | A61B 1/00009 348/65 |
| 2015/0348253 A1* | 12/2015 | Bendall | G06T 7/0004 348/86 |
| 2016/0071547 A1* | 3/2016 | Sugawara | G06F 19/321 386/241 |

FOREIGN PATENT DOCUMENTS

| | | |
|---|---|---|
| JP | 2010-034763 A | 2/2010 |
| JP | 2010-206367 A | 9/2010 |
| JP | 2012-045419 A | 3/2012 |
| JP | 2013-138492 A | 7/2013 |
| JP | 2014-060499 A | 4/2014 |

* cited by examiner

IMAGE PLAYBACK APPARATUS AND COMPUTER-READABLE RECORDING MEDIUM

CROSS-REFERENCE TO RELATED APPLICATIONS

This application is a continuation of PCT international application Ser. No. PCT/JP2015/082874 filed on Nov. 24, 2015 which designates the United States, incorporated herein by reference, and which claims the benefit of priority from Japanese Patent Application No. 2014-240172, filed on Nov. 27, 2014, incorporated herein by reference.

BACKGROUND

1. Technical Field

The disclosure relates to an image playback apparatus and a computer-readable recording medium for playing back of moving image data recorded on a recording device.

2. Related Art

As a known art in the medical field, an endoscope system is used for examining internal portions of a subject. The endoscope system typically inserts a flexible insertion unit having a thin and long shape into a subject such as a patient, emits illumination light from a distal end of the insertion unit, and receives reflected light of the illumination light, on an imaging unit of the distal end of the insertion unit, thereby sequentially capturing an in-vivo image. A plurality of sequential in-vivo images captured in this manner undergoes predetermined image processing on a processing device and thereafter, is displayed on a display of the endoscope system substantially in real time, as a video image in a moving image format. A physician, or the like, performs examination while observing internal biological portions through the video image displayed on the display.

In recent years, there is proposed a technique capable of also generating still image data of a desired site while recording a captured biological image in a moving image format during endoscopic examination (for example, refer to JP 2012-45419 A). In this technique, when a release button provided on an operating unit of an endoscope is pressed, a processing device generates still image data corresponding to a timing of pressing the release button, and records the generated still image data in association with moving image data.

SUMMARY

In some embodiments, an image playback apparatus includes: a data input unit into which moving image data as a playback target, among moving image data recorded on a recording device, is input; a moving image processing unit configured to generate playback-oriented moving image data from the moving image data input from the data input unit; a display controller configured to play back, on a display device, the playback-oriented moving image data generated by the moving image processing unit; a release instruction input unit configured to receive input of a release signal during playback of the playback-oriented moving image data; a still image generation unit configured to generate, from the moving image data, still image data that correspond to a playback image being played back on the display device at a time of input of the release signal; and a recording controller configured to: record, on the recording device, the still image data generated by the still image generation unit, in association with the moving image data; and record input information of a release signal in association with the moving image data when the release signal is input during recording of the moving image data. The display controller is configured to: display, on the display device, playback position information that indicates a playback position of an image being played back on the display device among a bundle of the moving image data linearly arranged in time series; and display, on the playback position information, a first mark that indicates an input timing of the release signal input during playback of the moving image data, and a second mark that has a different display mode from the display mode of the first mark and that indicates an input timing of the release signal based on the input information recorded in association with the moving image data.

In some embodiments, a non-transitory computer-readable recording medium recording an image playback program is provided. The program causes an image playback apparatus for playing back, on a display device, moving image data as a playback target from among moving image data recorded on a recording device to execute: generating playback-oriented moving image data from the moving image data as the playback target; playing back, on the display device, the generated playback-oriented moving image data; displaying, on the display device, playback position information that indicates a playback position of an image being played back on the display device among a bundle of the moving image data linearly arranged in time series; displaying, on the playback position information, a first mark that indicates an input timing of the release signal input during playback of the moving image data, and a second mark that has a different display mode from the display mode of the first mark and that indicates an input timing of the release signal based on the input information recorded in association with the moving image data; receiving input of a release signal during playback of the playback-oriented moving image data; generating, from the moving image data, still image data that correspond to a playback image being played back on the display device at a time of input of the release signal; recording, on the recording device, the generated still image data, in association with the moving image data; and when the release signal is input during recording of the moving image data, recording input information of a release signal in association with the moving image data.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, an endoscope system will be described according to embodiments of the present invention (hereinafter, referred to as "embodiment(s)"). Note that the present invention is not intended to be limited by these embodiments. In the description of the drawings, same reference signs are attached to the same portions.

Embodiments

Figure 1:
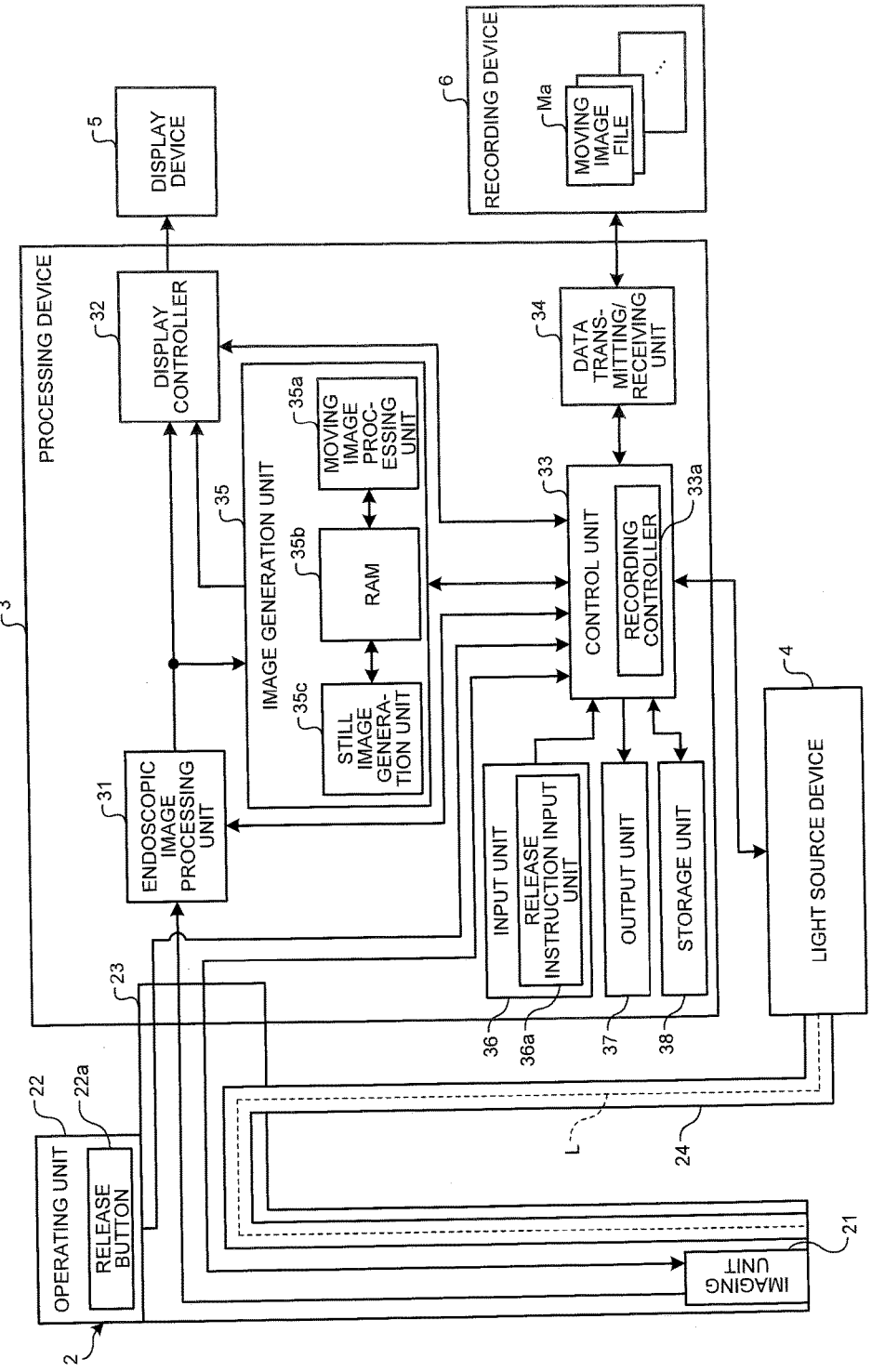
FIG. 1 is a block diagram schematically illustrating a configuration of an endoscope system according to the disclosure.

FIG. 1 is a block diagram schematically illustrating a configuration of an endoscope system.

As illustrated in FIG. 1, an endoscope system 1 according to the first embodiment includes an endoscope 2 (scope), a processing device 3 (image playback apparatus), a light source device 4, a display device 5, and a recording device 6. The endoscope 2 (scope) is introduced into a subject, images an internal portion of the subject, and sequentially generates image data of the internal portion of the subject. The processing device 3 (image playback apparatus) performs predetermined image processing on the image data sequentially captured by the endoscope 2 and the moving image data input from the recording device 6, and controls components of the endoscope system 1. The light source device 4 generates illumination light (observation light) L for the endoscope 2. The display device 5 includes a display using liquid crystal or organic electro luminescence (EL) and displays various images including moving image data that have undergone image processing performed by the processing device 3. The recording device 6 records a plurality of moving image files Ma including moving image data of an internal body portion captured by the endoscope 2 and additional information of the moving image data.

The endoscope 2 includes an imaging unit 21, an operating unit 22, a connector 23, and a light guide cable 24. The imaging unit 21 captures an image of an internal portion (in-vivo image) of the subject. The operating unit 22 is gripped by an operator. The connector 23 is arranged on a proximal end of the endoscope 2 and is removably connected to a connector on the processing device 3. The light guide cable 24 supplies the illumination light L generated by the light source device 4 to a distal end of the endoscope 2. The imaging unit 21 includes an optical system including an objective lens, and one of a CCD image sensor and a CMOS image sensor. The imaging unit 21 is arranged at the distal end of the endoscope 2. The operating unit 22 includes a bending knob, a treatment instrument insertion unit, and a plurality of buttons. The bending knob is used to bend the endoscope 2. The plurality of buttons is used to operate peripheral equipment such as the processing device 3, the light source device 4, an air feeding device, a water feeding device, and a gas feeding device. The operating unit 22 includes a release button 22a. In a case where the release button 22a is pressed during endoscopic examination, the operating unit 22 inputs a mid-examination release signal to a control unit 33 of the processing device 3, to be described below. The mid-examination release signal issues an instruction to generate still image data (release image data) from the image displayed on the display device 5 when the release button 22a is pressed. Under the control of the control unit 33, an image generation unit 35 to be described below generates, in response to the input of the mid-examination release signal, release image data based on the image displayed on the display device 5 at the input timing of the mid-examination release signal.

The processing device 3 includes an endoscopic image processing unit 31, a display controller 32, the control unit 33, a data transmitting/receiving unit 34, the image generation unit 35, an input unit 36, an output unit 37, and a storage unit 38.

The endoscopic image processing unit 31 performs, on the image data input from the endoscope 2, various image processing including clamp processing, noise reduction processing, gain adjustment processing, analog/digital (A/D) conversion processing, optical black subtraction processing, image data synchronization processing, gamma correction processing, white balance (WB) adjustment processing, color matrix computing processing, color reproduction processing, edge emphasis processing, enlargement and reduction processing, superpose processing of display data such as textual data input from the input unit 36, and picture-in-picture processing. A series of continuous endoscopic image data is sequentially input from the endoscope 2. The endoscopic image processing unit 31 outputs the image-processed endoscopic image data to the display controller 32 and the image generation unit 35.

Based on the input image data, the display controller 32 generates display-oriented image data to be displayed on the display device 5 and outputs the data to the display device 5. A display-oriented image signal to be output to the display device 5 includes, for example, digital signals of SDI, DVI, and HDMI (registered trademark) formats. Alternatively, the display controller 32 may convert the display-oriented image signal from a digital signal to an analog signal, change the converted analog image data into a format of high-vision system, or the like, and then, output the signal to the display device 5.

Figure 2:
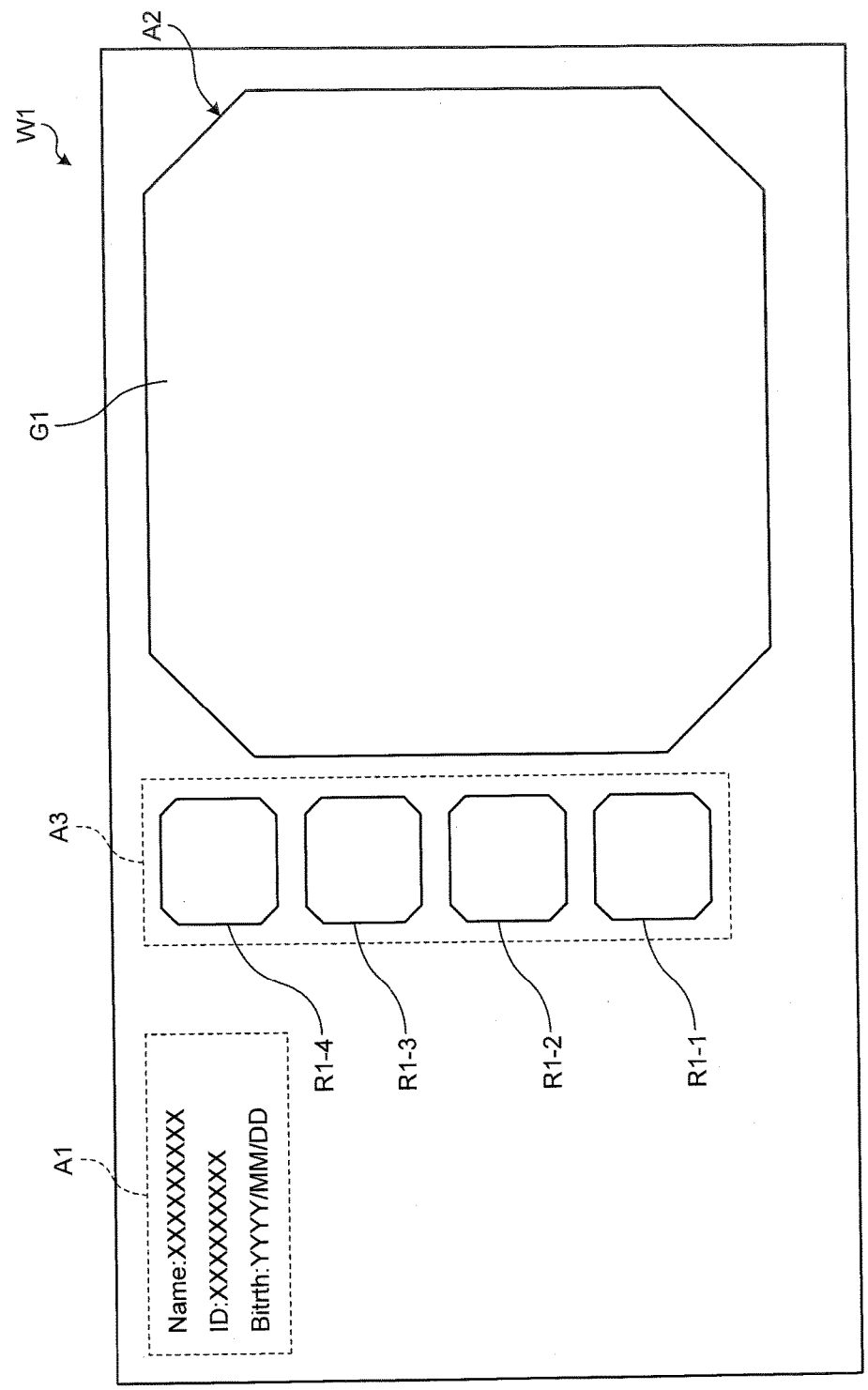
FIG. 2 is an exemplary display screen of a display device that displays a live video image under endoscopic examination.

In a case where endoscopic examination is under execution, the endoscopic image data that have undergone processing performed by the endoscopic image processing unit 31 are input into the display controller 32. Accordingly, an examination image obtained by the endoscope 2 is displayed on the display screen of the display device 5, as a live video image. FIG. 2 is an exemplary display screen of the display device 5 that displays a live video image under endoscopic examination. As illustrated in FIG. 2, a window W1 for examination image display is displayed on the display screen of the display device 5. The window W1 is configured to include a region A1 on an upper-left portion, a region A2 on the right side, and a region A3 around the central portion. The region A1 displays information on the subject (patient), for example, name, ID, date of birth. The region A2 displays an in-vivo image G1 under imaging by the endoscope 2. The region A3 displays, as a scene-index, each of release images R1-1 to R1-4 generated in response to pressing of the release button 22a during the endoscopic examination. The release images R1-1 to R1-4 are displayed sequentially on the region A3 from top to bottom, beginning from the release image having smallest difference of timings, namely, the imaging timing of the in-vivo image G1 actually displayed in the region A2, and the input timing of the mid-examination release signal on each of the release images. The release images R1-1 to R1-4 are displayed on the window W1 in a state reduced from an actual size.

In a case where an instruction for playback of specific endoscopic examination moving image data recorded on the recording device 6 is issued, playback-oriented moving image data are input into the display controller 32 from a moving image processing unit 35a of the image generation unit 35 to be described below. As a result, the moving image data of a past endoscopic examination, to which a playback instruction has been issued, are displayed as a playback video image on the display screen of the display device 5.

The control unit 33 includes a CPU. The control unit 33 controls processing operation of components of the processing device 3. The control unit 33 controls operation of the processing device 3 by performing transfer, or the like, of instruction information or data toward the constituents of the processing device 3. The control unit 33 is connected, via individual cables, to the constituent sites of the imaging unit 21 and the light source device 4, and to the display device 5. The control unit 33 controls operation of the imaging unit 21, the light source device 4, and the display device 5, as well. The control unit 33 includes a recording controller 33a. The recording controller 33a is connected to the recording device 6 via the data transmitting/receiving unit 34 to be described below, and performs data recording control toward the recording device 6. In a case where an instruction for playback of certain moving image data recorded on the recording device 6 is issued via the input unit 36, the control unit 33 receives the moving image data as a playback target from the recording device 6 via the data transmitting/receiving unit 34, and inputs the data into the image generation unit 35. In this case, the control unit 33 obtains additional information including mid-examination release signal input information and release image data, associated with the moving image data as a playback target, together with the playback-oriented moving image data, and outputs the obtained data and information to the display controller 32 and the image generation unit 35.

The data transmitting/receiving unit 34 is an interface connectable to a portable recording medium including a USB memory, an image recording device, and a video image recording device, or communication lines such as wired LAN and wireless LAN, and includes a USB port and a LAN port. In an embodiment, the data transmitting/receiving unit 34 is connected to the recording device 6, and performs, under the control of the control unit 33, transmission and reception of various data including moving image data and additional information related to the moving image data, between the own unit and the recording device 6.

The image generation unit 35 performs processing related to the moving image data and release image generation processing. The image generation unit 35 includes the moving image processing unit 35a, RAM 35b, and a still image generation unit 35c. The RAM 35b temporarily stores data under processing on the image generation unit 35.

In a case where endoscopic examination is under execution, the moving image processing unit 35a generates moving image data corresponding to this endoscopic examination. The moving image processing unit 35a generates (with encoding) moving image data having a predetermined format from a series of continuous endoscopic image data input on the endoscopic image processing unit 31, and outputs the generated data to the control unit 33. In a case where an instruction for playback of certain moving image data recorded on the recording device 6 is issued, the moving image processing unit 35a generates playback-oriented moving image data to be displayed on the display device 5 by converting the format of the moving image data as a playback target input from the recording device 6 via the data transmitting/receiving unit 34 and the control unit 33, into a display-oriented format. The moving image processing unit 35a outputs the generated playback-oriented moving image data to the display controller 32. The moving image processing unit 35a includes an image processing circuit including an encoding-decoding circuit.

In a case where the input of the release signal has been received, the still image generation unit 35c generates release image data corresponding to the image displayed on the display device 5 at the time of input of the release signal. In a case a mid-examination release signal is input from the operating unit 22 by pressing of the release button 22a during endoscopic examination, the still image generation unit 35c generates mid-examination release image data from the endoscopic image data displayed on the display device 5 at the timing of input of the mid-examination release signal, among endoscopic image data input from the endoscopic image processing unit 31. In a case where a mid-playback release signal is input from a release instruction input unit 36a to be described below by operation of an input device by an operator during playback of moving image data of endoscopic examination, the still image generation unit 35c generates mid-playback release image data corresponding to the playback image that is being played back on the display device 5 at the time of input of the mid-playback release signal, and outputs the generated data to the control unit 33. The still image generation unit 35c includes an image processing circuit including an encoding-decoding circuit.

On the above-described control unit 33, the recording controller 33a records moving image data of endoscopic examination onto the recording device 6 via the data transmitting/receiving unit 34. The moving image data of endoscopic examination are data that have been output from the moving image processing unit 35a of the image generation unit 35. In a case where the release button 22a is pressed by an operator during endoscopic examination, namely, during recording of the moving image data, the recording controller 33a records a moving image file Ma onto the recording device 6. The moving image file Ma has associated input information on mid-examination release signal input by pressing of the release button 22a and mid-examination release image data generated in response to the input of the mid-examination release signal, with the moving image data corresponding to the endoscopic examination. In addition, in a case where a mid-playback release signal has been input from the release instruction input unit 36a during playback of the moving image data corresponding to the endoscopic examination, the recording controller 33a further associates input information of the mid-playback release signal and the mid-playback release image data generated in response to the input of the mid-playback release signal, with the moving image data as a playback target on the recording device 6, and records the associated information and data.

The input unit 36 includes an input device such as a mouse, a keyboard, and a touch panel, and receives input of various kinds of instruction information. Specifically, the input unit 36 receives input of various instruction information including information on the subject under examination with the endoscope 2 (for example, ID, date of birth, and name), identification information of the endoscope 2 (for example, ID and examination items), and details of examination. The input unit 36 includes a release instruction input unit 36a, which receives input of the mid-playback release signal during the period of playback of the playback-oriented moving image data on the display device 5. The mid-playback release signal is a signal that issues instruction for generating the mid-playback release image data. The release instruction input unit 36a includes a release icon and a pointing device. The release icon is displayed within a moving image playback window of the display device 5. The pointing device can be used to select the release icon. Alternatively, of course, it is allowable to have a configuration in which the mid-playback release signal can be input by pressing of the release button 22a on the operating unit 22 described above, and the mid-examination release signal can be input by the release instruction input unit 36a.

The output unit 37 includes a speaker and a printer. According to the control of the control unit 33, the output unit 37 outputs information regarding display processing of a live video image of the endoscopic image data, or regarding playback processing of the moving image data recorded on the recording device 6.

The storage unit 38 includes volatile memory and non-volatile memory, and stores various programs for operating the endoscope 2, the processing device 3, the light source device 4, and the display device 5. The storage unit 38 is also capable of storing various image data processed by the processing device 3 and additional information. The storage unit 38 can also be formed with a memory card, or the like, attached from outside of the processing device 3.

Figure 3:
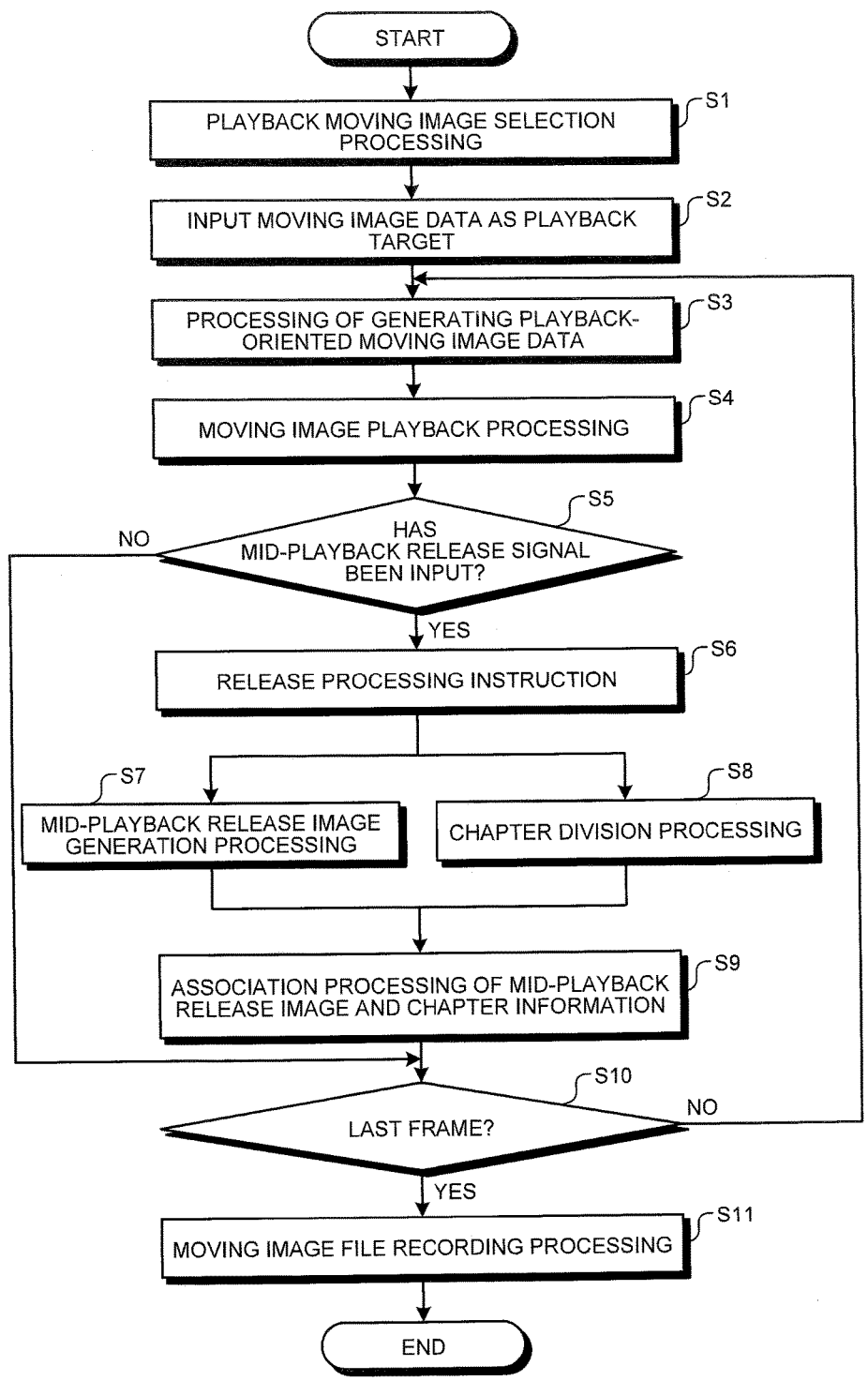
FIG. 3 is a flowchart illustrating a processing procedure until the processing device illustrated in FIG. 1 plays back moving image data as a playback target, on the display device.

FIG. 3 is a flowchart illustrating a processing procedure until the processing device 3 plays back moving image data as a playback target on the display device 5. Processing in FIG. 3 is executed in a case where endoscopic examination moving image data recorded during endoscopic examination are watched for review after examination when an operator such as a physician is going to prepare an examination report after completion of the endoscopic examination.

As illustrated in FIG. 3, playback moving image selection processing is first performed (step S1) on the processing device 3. In the playback moving image selection processing, by operation of an input device by an operator selection information for selecting moving image data as a playback target, from among individual moving image data recorded on the recording device 6, is input from the input unit 36.

Figure 4:
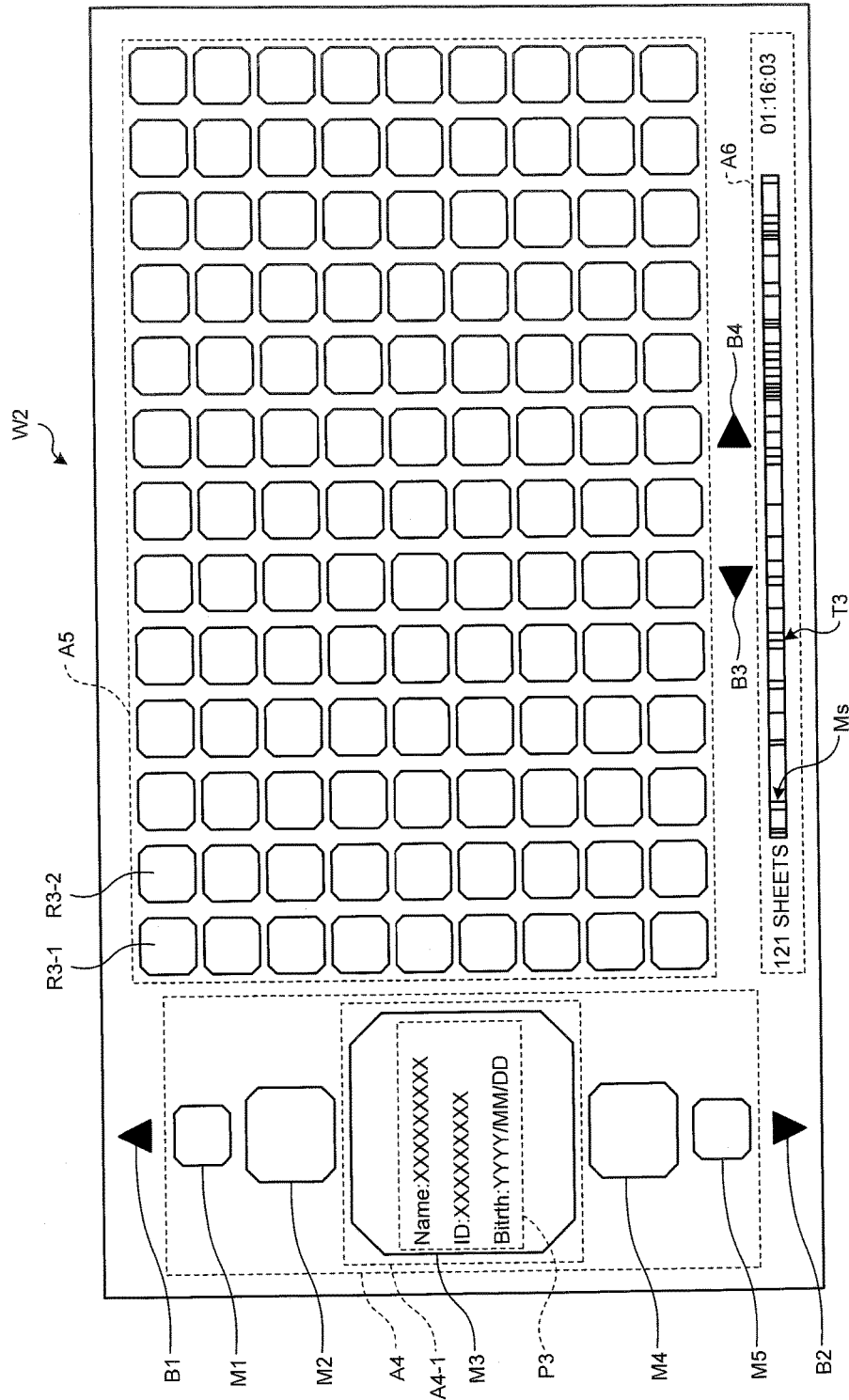
FIG. 4 is an exemplary moving image selection screen displayed on the display device illustrated in FIG. 1.

The playback moving image selection processing is configured such that the display controller 32 first displays a moving image selection screen on the display device 5 under the control of the control unit 33. The moving image selection screen is used for selecting moving image data as a playback target among a plurality of moving image data recorded on the recording device 6. FIG. 4 is an exemplary moving image selection screen displayed on the display device 5.

As illustrated in FIG. 4, a moving image selection screen W2 is configured to include a region A4 on the left side, a large region A5 on center to right portions, and a region A6 at the bottom. The region A4 displays representative images for identifying selectable moving image data M1 to M5, arranged in a line in the order of individual moving image data M1 to M5. The moving image data whose representative image is displayed on a center region A4-1 are treated as candidate moving image data for selection and displayed more largely than the representative images for the other moving image data. The representative image of the moving image data M3 displayed in the center region A4-1 displays patient information P3 (for example, ID, name, date of birth) that corresponds to moving image data M3, superposed onto the image. The representative image can be set arbitrarily, for example, can be set to the first image in the third chapter of the moving image data. A moving image selection page backward icon B1 is displayed on a top portion of the region A4, and a moving image selection page forward icon B2 is displayed on a bottom portion of the region A4. By selecting one of the icons B1 or B2, the operator can change the moving image data displayed in the region A4 to the next or previous data. The region A5 displays thumbnail images of mid-examination release images (R3-1, R3-2, . . . ) of the moving image data M3 displayed in the center region A4-1, in a matrix form in an order of input of the mid-examination release signals. A release image backward icon B3 and a release image forward icon B4 are displayed below the region A5. By selecting one of the icons B3 and B4, the operator can change the mid-examination release image displayed in the region A5 to the next or previous image, respectively.

Figure 5:
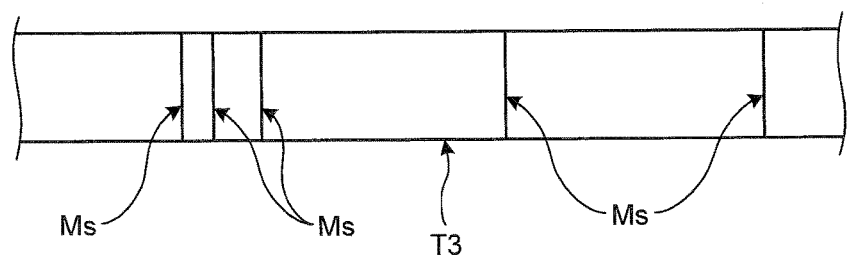
FIG. 5 is a partial enlargement diagram of a seek bar illustrated in FIG. 4.

The region A6 displays a seek bar T3 for the moving image data M3, for which the representative image is displayed in the central region A4-1. The seek bar T3 represents playback position information indicating a playback position of an image being played back on the display device 5, among bundles of the moving image data M3 linearly arranged in time series. The seek bar T3 displays, on its right, an examination period for the moving image data M3, and displays, on its left, the total number of mid-examination release images generated for the moving image data M3 during endoscopic examination. FIG. 5 is a partial enlargement diagram of the seek bar T3 illustrated in FIG. 4. As illustrated in FIG. 5, a vertical bar-shaped mark Ms is indicated within the seek bar T3. The mark Ms represents each of input timings of the mid-examination release signals during an examination period.

By visually recognizing the moving image selection screen W2, the operator can select the moving image data as a playback object while confirming candidate moving image data, the mid-examination release image associated with the moving image data, and the input timing of the mid-examination release signal, and thus, can easily find the moving image data as a playback object. When the representative image of the moving image data as a playback object is selected by operation of the input device by the operator, the input unit 36 inputs selection information into the control unit 33. This selection information includes information in which the moving image data corresponding to the representative image has been selected as the moving image data as a playback target.

Figure 6:
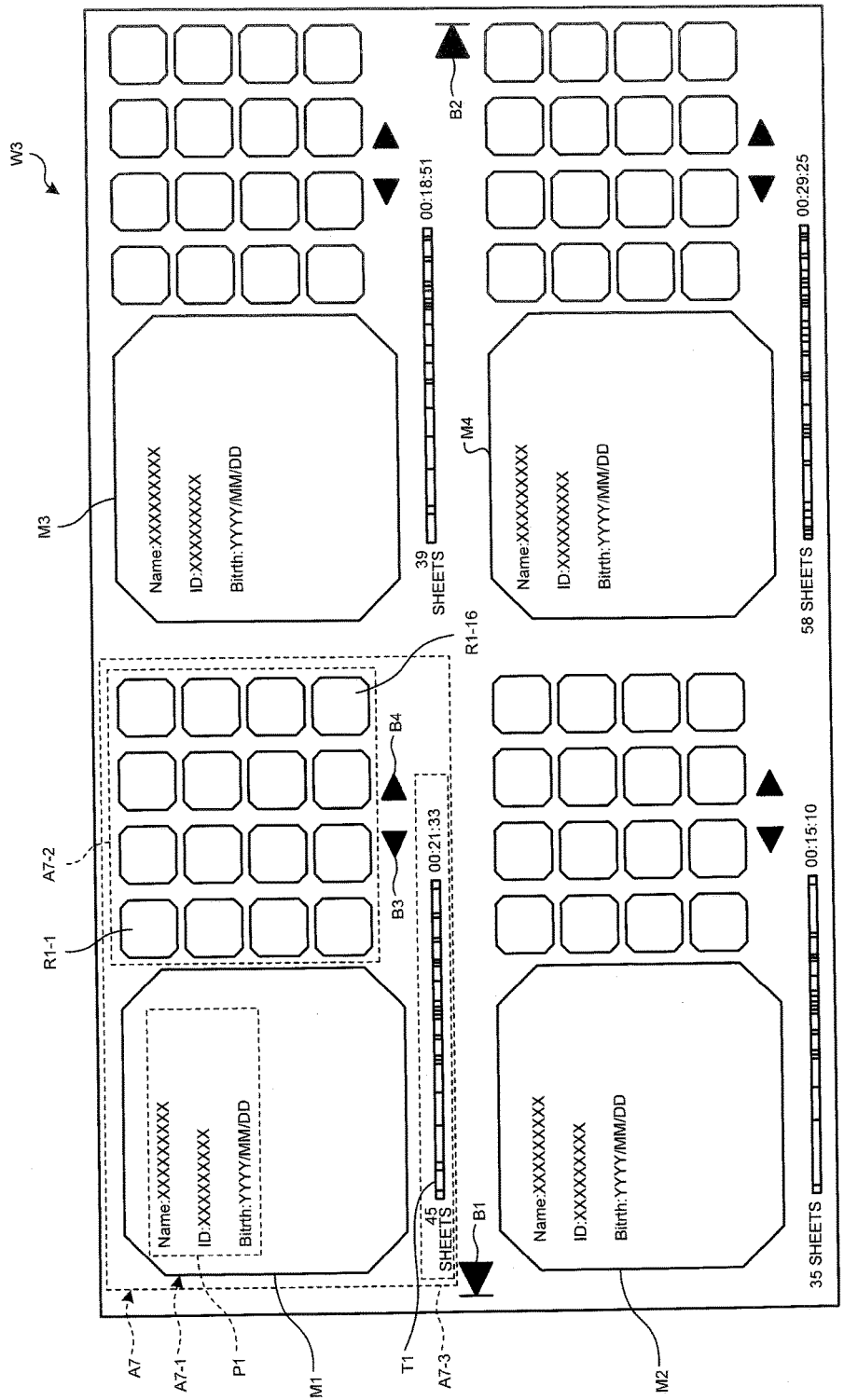
FIG. 6 is another exemplary moving image selection screen displayed on the display device illustrated in FIG. 1.

Alternatively, in step S1, the display controller 32 may display, on the display device 5, a moving image selection screen W3 illustrated in FIG. 6. For example, the moving image selection screen W3 may be divided into four regions, and each of the divided regions may display a representative image for each of the moving image data M1 to M4, a thumbnail image of the mid-examination release image, and a seek bar.

For example, the region A7 on the moving image selection screen W3 corresponds to moving image data M1, and a representative image of the moving image data M1 is displayed in a region A7-1 among the region A7, thumbnail images of mid-examination release images R1-1 to R1-16 of the moving image data M1 are displayed in a region A7-2, and the seek bar T1 of the moving image data M1 is displayed in a region A7-3. The representative image in the region A7-1 displays patient information P1 of the moving image data M1, superposed onto the image. The release image backward icon B3 and a release image forward icon B4 are displayed, below the region A7-2. With the icons B3 and B4, it is possible to select forward and backward operation of the mid-examination release image. The left end and right end portions of the moving image selection screen W3 display the moving image selection page backward icon B1 and the moving image selection page forward icon B2, capable of selecting backward and forward operation of each of the moving image data displayed on the screen. Even in visually recognizing the moving image selection screen W3, the operator can select the moving image data as a playback object while confirming the mid-examination release image associated with the candidate moving image data, and the input timing of the mid-examination release signal.

Under the control of the control unit 33, the moving image data for which a playback instruction has been issued by selection information is input (step S2) from the recording device 6 to the data transmitting/receiving unit 34. In this case, moving image data as a playback target, and together with this, input information of the mid-examination release signal associated with the moving image data, and the mid-examination release image data are also input from the recording device 6. The data transmitting/receiving unit 34 inputs moving image data into the image generation unit 35 via the control unit 33, and together with this, inputs information of mid-examination release signal associated with the moving image data, and the mid-examination release image data into the display controller 32.

The image generation unit 35 is configured such that the moving image processing unit 35a generates playback-oriented moving image data from the input moving image data and performs processing (step S3) of generating playback-oriented moving image data to be output onto the display controller 32. The display controller 32 performs moving image playback processing (step S4) that displays the input playback-oriented moving image data on the display device 5.

Figure 7:
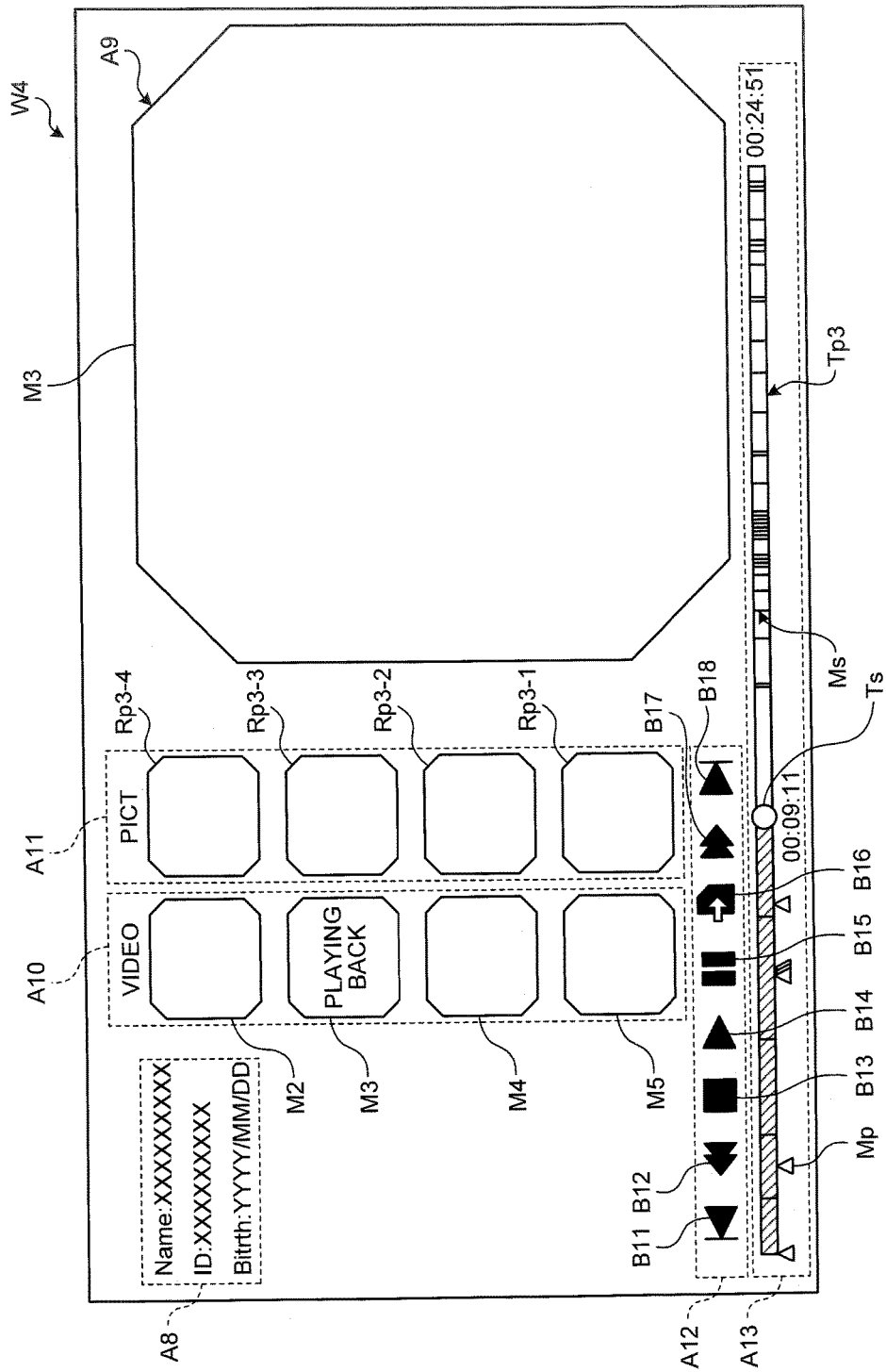
FIG. 7 is an exemplary display screen of a display device that displays a moving image of endoscopic examination.

FIG. 7 is an exemplary display screen of the display device 5 that displays a moving image of endoscopic examination. In step S4, the display screen of the display device 5 displays, for example, a window W4 for examination image playback illustrated in FIG. 7.

The window W4 is configured to include a region A8 in upper-left portion, a region A9 on the right side, a region A10 in a center left portion, a region A11 on the right side of the region A10, a region A12 in a lower-left side, and a region A13 at the bottom. The patient information region A8 displays patient information. Moving image data to which playback instruction has been issued are played back in the region A9. The region A10 displays representative images of the moving image data M2 to M5, arranged in a line. FIG. 7 illustrates a case where the moving image data M3 among these are played back in the region A9. In the region A11, four mid-playback release images Rp3-1 to Rp3-4 to which release instructions have been issued during playback of the moving image data M3 in the region A9 are displayed sequentially from top to bottom, in an order from the smaller level of difference between the imaging timing of the moving image data currently being played back in the region A9, and the input timing of the mid-playback release signal among the mid-playback release images.

The region A12 displays icon images to control image display. The icon images include a jump to first frame icon B11, a chapter backward icon B12, a stop icon B13, a playback icon B14, a pause icon B15, a release icon B16, a chapter forward icon B17, and jump to last frame icon B18. As described above, the release icon B16 is included in the release instruction input unit 36a. When the release icon B16 is selected during playback of moving image data in the region A9, a mid-playback release signal is input into the control unit 33. As a result, a mid-playback release image corresponding to the playback image being displayed in the region A9 at the time of selection of the release icon B16 is generated by the still image generation unit 35c, and the generated image is recorded by the recording controller 33a, in association with the moving image data M3. Together with this, the mid-playback release image at the lowermost position on the column is deleted in the region A11, causing the other mid-playback release images to step down by one sheet. This allows a newly generated mid-playback release image to be arranged at the head of the column.

The region A13 displays a seek bar Tp3 for the moving image data M3 being played back in the region A9. The portion on the right side of the seek bar Tp3 displays a whole examination period for the moving image data M3. The seek bar Tp3 displays a slider Ts, which indicates playback position in the entire moving image data M3 of the image being currently played back in the region A9.

Figure 8:
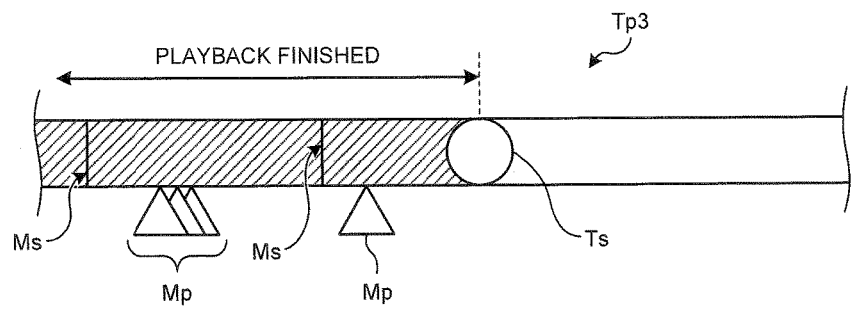
FIG. 8 is a partial enlargement diagram of a seek bar illustrated in FIG. 7.

FIG. 8 is a partial enlargement diagram of the seek bar Tp3 illustrated in FIG. 7. As illustrated in FIG. 8, the slider Ts is displayed on the seek bar Tp3 to indicate a playback position of the image being played back on the display device 5. The left-side portion on the slider Ts corresponding to a playback-finished period is displayed in a color or pattern different from the non-played-back period on the right side of the slider Ts. Similarly to FIG. 5, a vertical bar-shaped mark Ms is indicated within the seek bar Tp3. The mark Ms indicates an input timing of each of the mid-examination release signals during an examination period. In addition, at a lower end of the seek bar Tp3, an open triangle mark Mp is displayed. The mark Mp indicates an input timing of the mid-playback release signal input during playback of the moving image data M3. In the present embodiment, the display mode of the mark Ms corresponding to the mid-examination release signal is made different from the display mode of the mark Mp corresponding to the mid-playback release signal. This difference makes it possible to distinguish the timing corresponding to the mid-examination release signal from the timing corresponding to the mid-playback release signal. When the mark Ms on the seek bar Tp3 is tapped, the playback position of the moving image data M3 being played back in the region A9 moves to the position of input of the mid-examination release signal corresponding to the tapped mark Ms. In addition, the mid-playback release image displayed in the region A11 is also switched to the latest mid-playback release image corresponding to the playback position. Similarly, when the mark Mp on the seek bar Tp3 is tapped, the playback position of the moving image data M3 being played back in the region A9 moves to the position of input of the mid-playback release signal corresponding to the tapped mark Mp. In a case where playback of the moving image data M3 is the second time, it would be sufficient to change the display mode of the marks indicating the input timing of the mid-playback release signals, from each other, namely, between the first-time playback and second-time playback.

The control unit 33 determines (step S5) whether the mid-playback release signal has been input from the release instruction input unit 36a by selection of the release icon B16 described above. In a case where the control unit 33 determines that the mid-playback release signal has been input (step S5: Yes), the control unit 33 issues a release processing instruction (step S6). In response to this instruction, the still image generation unit 35c performs mid-playback release image generation processing, that is, generates mid-playback release image data that corresponds to the playback image at the time of input of the mid-playback release signal, and outputs the generated data to the control unit 33 (step S7). The recording controller 33a performs chapter division processing, in which the moving image data M3 during playback are divided in chapters at the input timing of the mid-playback release signal (step S8). Step S7 and step S8 are parallel processing.

Figure 9:
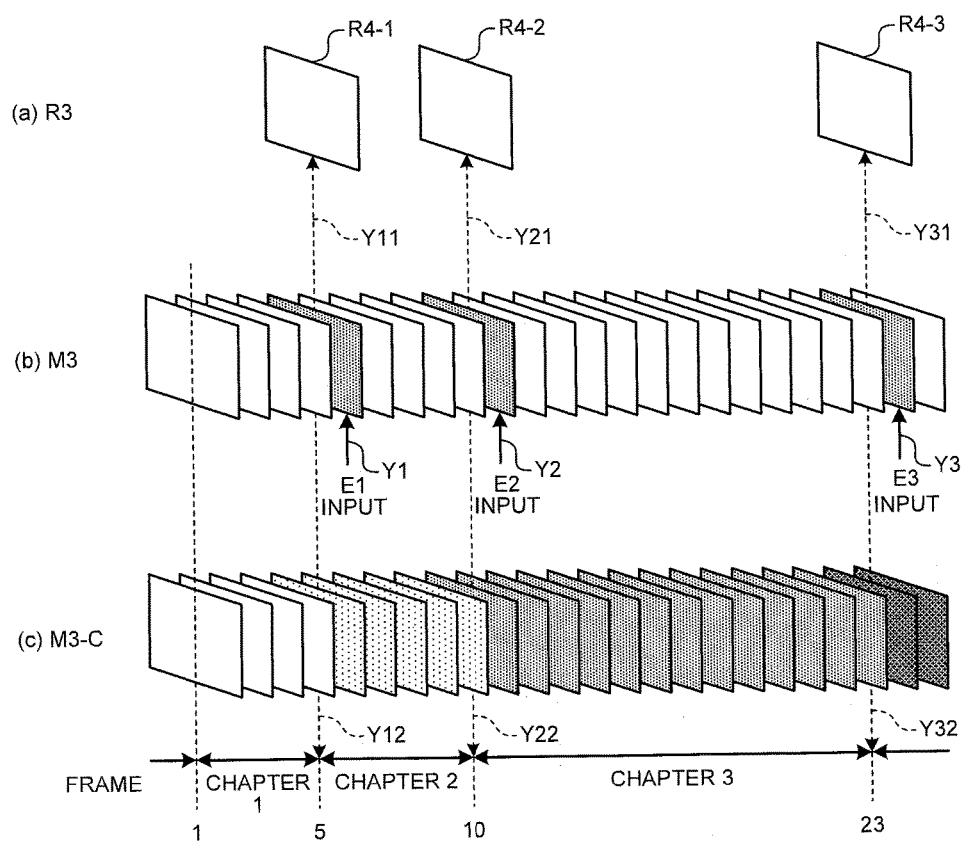
FIG. 9 is a schematic diagram illustrating mid-playback release image data generation processing and chapter division processing, illustrated in FIG. 3.

FIG. 9 is a schematic diagram illustrating processing of step S7 and step S8, illustrated in FIG. 3. Specifically, (a) of FIG. 9 is a diagram illustrating processing of generating mid-playback release image data of the moving image data M3 by the still image generation unit 35c; (b) of FIG. 9 is a schematic diagram illustrating a portion of frames of the moving image data M3 as a playback target arranged in an order of frames; and (c) of FIG. 9 is a schematic diagram illustrating a portion of frames of the moving image data M3-C after chapter division, arranged in an order of frames. Each of (b) and (c) of FIG. 9 illustrates frames from a first frame to a 24th frame of each of the moving image data M3 and M3-C, respectively.

As illustrated by arrow Y1 in (b) of FIG. 9, a case where a mid-playback release signal E1 is input when a fifth-frame image among the moving image data M3 is being played back will be described. In this case, the still image generation unit 35c, as illustrated by arrow Y11, generates mid-playback release image data R4-1 (refer to (a) of FIG. 9) that correspond to the fifth-frame image being played back at the input timing of the mid-playback release signal E1. Along with this, as illustrated by arrow Y12, the recording controller 33a divides the moving image data M3 currently in playback such that the frames from the first frame to the fourth frame become chapter 1 (refer to (c) of FIG. 9). This means the recording controller 33a performs chapter division such that the fifth-frame image being played back at the input timing of the mid-playback release signal E1 becomes a first frame of chapter 2.

As illustrated by arrow Y2 in (b) of FIG. 9, in a case where a next mid-playback release signal E2 is input at playback of a 10th frame image, the still image generation unit 35c generates, as illustrated by arrow Y21, a mid-playback release image data R4-2 (refer to (a) of FIG. 9) corresponding to the 10th frame image, and the recording controller 33a divides the moving image data M3 during playback, as illustrated by arrow Y22, such that the frames from fifth frame to ninth frame become chapter 2 (refer to (c) of FIG. 9). Similarly, as illustrated by arrow Y3 in (b) of FIG. 9, in a case where a mid-playback release signal E3 is input at playback of a 23th frame image, the still image generation unit 35c generates, as illustrated by arrow Y31, a mid-playback release image data R4-3 (refer to (a) of FIG. 9) corresponding to the 23th frame image, and the recording controller 33a divides the moving image data M3 during playback, as illustrated by arrow Y32, such that the frames from 10th frame to 22th frame become chapter 3 (refer to (c) of FIG. 9).

The recording controller 33a performs association processing (step S9) in which the mid-playback release image data generated in step S7 and the chapter information regarding the chapter divided in step S8 are associated with the moving image data M3, and temporarily stores each of associated data in the storage unit 38.

In a case where step S9 is finished, or the control unit 33 determines that the mid-playback release signal has not been input (step S5: No), the control unit 33 determines whether the played back image is the last frame (step S10). In a case where the control unit 33 determines that the played back image is not the last frame (step S10: No), the processing returns to step S3, and processing to generate playback-oriented moving image data for the next playback frame is executed on the moving image processing unit 35a.

In contrast, in a case where the control unit 33 determines that the played back image is the last frame (step S10: Yes), the recording controller 33a performs moving image file recording processing (step S11) on the moving image data to which playback has finished. The moving image file recording processing records, onto the recording device 6, input information of the mid-playback release signal input during playback of this time, and the moving image file with which the mid-playback release image data generated by the still image generation unit 35c is associated.

Figure 10:
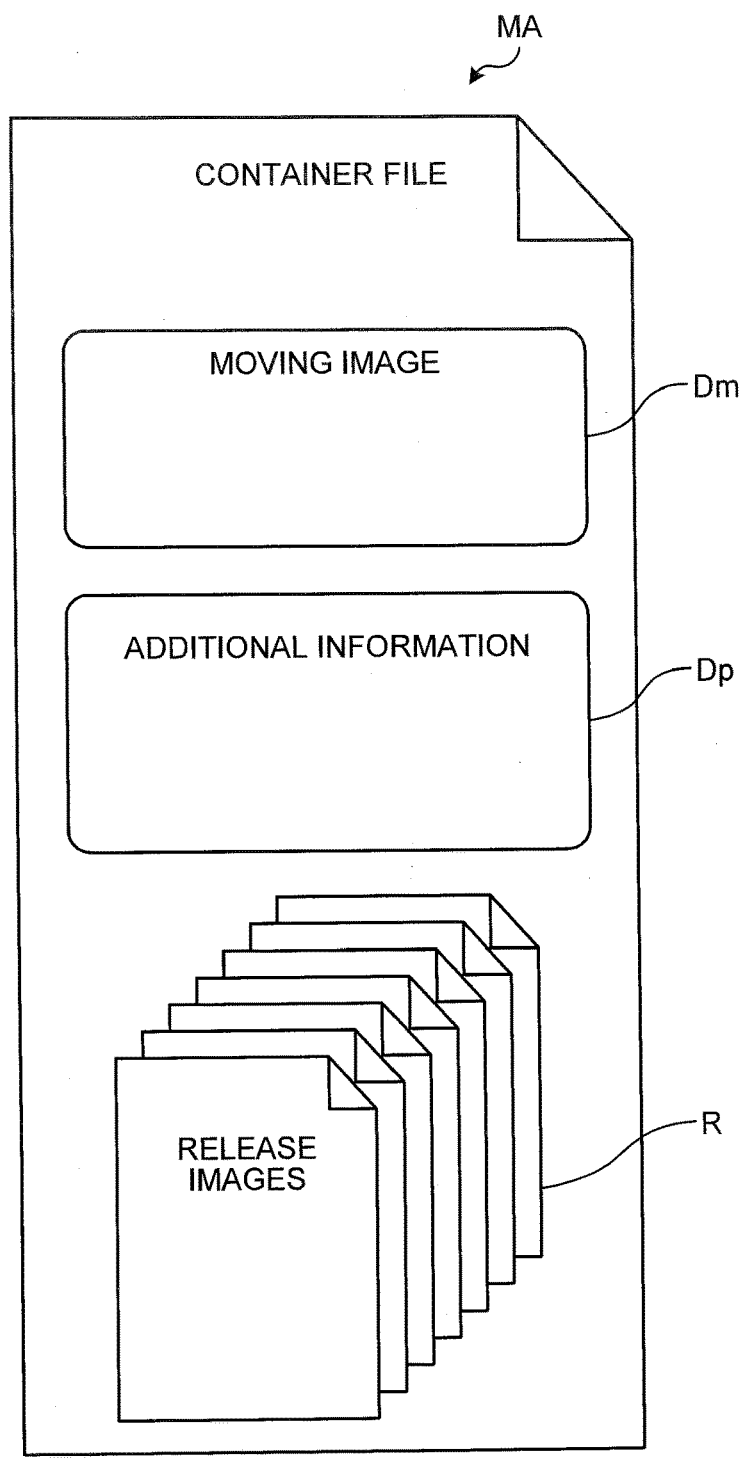
FIG. 10 is a diagram illustrating an exemplary configuration of a moving image file recorded by a recording controller illustrated in FIG. 1.

As illustrated in FIG. 10, the recording controller 33a records, in a single container file MA, the moving image data Dm, additional information Dp including input information on the mid-examination release signal and on the mid-playback release signal, chapter information, and sound data, and release image data R (mid-examination release image data and mid-playback release image data) generated by the still image generation unit 35c. In this case, it is possible to put all data regarding one examination into a single file, leading to facilitation of data management. Exemplary formats of the container file MA include mp4 and mov. Exemplary formats of the moving image data Dm include mpeg-1, mpeg-2, mpeg-4, and H264/AVC. Exemplary formats of the release image data R include jpeg, png, and tiff.

Figure 11:
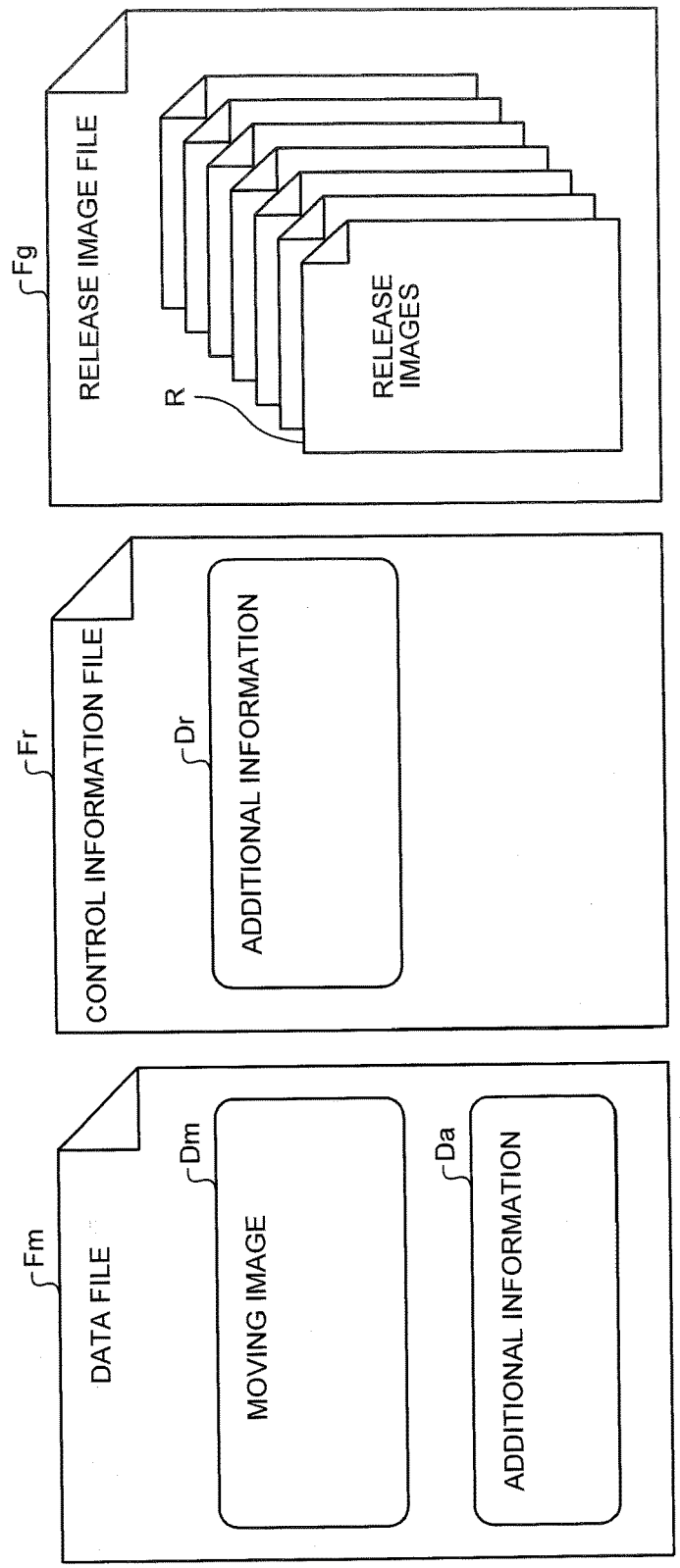
FIG. 11 is a diagram illustrating another exemplary configuration of the moving image file recorded by the recording controller illustrated in FIG. 1.

Alternatively, as illustrated in FIG. 11, the recording controller 33a may record the moving image data Dm and additional information Da including sound data, additional information Dr including chapter information or input information on release signal, and release image data R generated by the still image generation unit 35c, separately in a data file Fm, a control information file Fr, and a release image file Fg, respectively, and may associate the individual files with each other. In this case, any of the files can maintain versatility, and thus, it is possible on any of the servers to refer to moving image data, chapter information or release signal input information, and release image data. Exemplary data file formats Fm include avi and mpg. In step S11, the recording controller 33a records the moving image data in the recording device 6 in a state where the data are divided into chapters at the input timing of the mid-playback release signal. Input information of the mid-playback release signal corresponds to identification information of the divided chapters, or time information indicating the input timing of the mid-playback release signal. The additional information Da may include textual data input from the input unit 36, and it is allowable to superpose textual data onto the moving image data at playback of the moving image. With this data configuration, it is possible to display textual information with enhanced visibility regardless of the encoding compression rate in recording the moving image.

In this manner, in the present embodiment, it is possible to obtain new mid-playback release image data not only during examination by the endoscope 2 but also during playback for review of recorded moving image data obtained in endoscopic examination. For example, in the present embodiment, even in a case where a release image obtained in an endoscopic examination contains blur or defocusing due to pulsation and is hardly usable as diagnosis data, it is possible to newly obtain a release image suitably representing a desired position, during playback of the moving image data. With this configuration, according to the present embodiment, it is possible to suitably obtain a release image needed for diagnosis, and thus, to assist smooth diagnosis. Moreover, according to the present embodiment, it is possible to obtain a release image even during playback of the moving image data, reducing necessity of acquiring release image data during endoscopic examination. Accordingly, the present embodiment makes it possible to simplify operator's operation needed for release image acquisition, and to reduce time needed for endoscopic examination, leading to achievement of highly efficient endoscopic examination.

Moreover, in an embodiment, at the time of moving image selection, the moving image selection screens W2 and W3 (refer to FIGS. 4 and 6) are displayed on the display device 5. Each of the moving image selection screens W2 and W3 displays representative images of selectable moving image data, and corresponding mid-examination release images. Accordingly, the operator can select moving image data while reviewing the release image corresponding to the moving image data, and thus, can easily find the moving image data as a playback target.

Also in an embodiment, the seek bar Tp3 is displayed at playback of the moving image data, similarly to the window W4 for examination image playback, and the seek bar Tp3 displays the mark Ms indicating the input timing of the mid-examination release signal and the mark Mp indicating the input timing of the mid-playback release signal. In an embodiment, when the marks Mp and Ms are tapped during playback of moving image data, the playback position of the moving image data moves to the input position of the release signal corresponding to each of the tapped marks Ms and Mp. Accordingly, just by tapping the marks Mp and Ms, the operator can easily detect and play back the scene to which the release image generation instruction is issued, namely, the scene needed to be reviewed for diagnosis.

The present embodiment has described, with reference to FIG. 3, processing of generating mid-playback release image data by the processing device 3 in a case where a mid-playback release signal is input, and together with this, described processing of dividing the moving image data during playback into chapters with the input timing of the mid-playback release signal and processing of recording the chapter information in association with the moving image data. Similar processing is executable even in an endoscopic examination. In other words, in a case where a mid-examination release signal is input during endoscopic examination, the processing device 3 is capable of generating a mid-examination release image data, and in addition to this, capable of dividing the moving image data as a recording target into chapters at the input timing of the mid-examination release signal, and capable of recording chapter information in association with the moving image data.

In the present embodiment, an exemplary case in which the processing device 3 connected with the endoscope 2 generates mid-playback release image data. However, it is not limited to this. Any processor that is connectable to a display device and a recording device and that includes the image generation unit 35 can perform playback of moving image data, generation of release image data at playback, and association processing of additional information with the moving image data.

The execution programs for individual processing to be executed in the processing device 3 according to the present embodiment may be recorded on a computer readable recording medium such as a CD-ROM, a flexible disk, a CD-R and a DVD in a format of a file that can be installed or executed, and may be provided. Alternatively, the program may be stored on a computer connected to a network such as the Internet and may be supplied by downloading the program via the network. It is also allowable to provide or distribute the program via a network including the Internet.

According to some embodiments, in a case where input of a release signal is received during playback of playback-oriented moving image data, generated from moving image data, it is configured to generate still image data corresponding to a playback image that is being played back on a display device at the time of input of the release signal, from the moving image data, and to record the generated still image data in association with the moving image data, in a recording device. As a result, it is possible to obtain new still image data even during playback of moving image data.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image playback apparatus comprising:
   a data input unit into which moving image data as a playback target, among moving image data recorded on a recording device, is input;
   a moving image processing unit configured to generate playback-oriented moving image data from the moving image data input from the data input unit;
   a display controller configured to play back, on a display device, the playback-oriented moving image data generated by the moving image processing unit;
   a release instruction input unit configured to receive input of a release signal during playback of the playback-oriented moving image data;
   a still image generation unit configured to generate, from the moving image data, still image data that correspond to a playback image being played back on the display device at a time of input of the release signal; and
   a recording controller configured to:
      record, on the recording device, the still image data generated by the still image generation unit, in association with the moving image data; and
      record input information of a release signal in association with the moving image data when the release signal is input during recording of the moving image data, wherein
   the display controller is configured to:
      display, on the display device, playback position information that indicates a playback position of an image being played back on the display device among a bundle of the moving image data linearly arranged in time series; and
      display, on the playback position information, a first mark that indicates an input timing of the release signal input during playback of the moving image data, and a second mark that has a different display mode from the display mode of the first mark and that indicates an input timing of the release signal based on the input information recorded in association with the moving image data.

2. The image playback apparatus according to claim 1, wherein the moving image data are a series of image data generated by an imaging unit at a distal end of an endoscope during endoscopic examination, and the moving image data are image data recorded, on the recording device, associated with input information of a release signal input during the endoscopic examination.

3. The image playback apparatus according to claim 1, wherein the recording controller is configured to record the moving image data onto the recording device in a state where the moving image data are divided into chapters at an input timing of the release signal.

4. The image playback apparatus according to claim 3, wherein input information of the release signal is one of identification information of each of the divided chapters and time information indicating the input timing of the release signal.

5. The image playback apparatus according to claim 1, wherein the recording controller is configured to record the moving image data, the input information of the release signal, and the still image data generated by the still image generation unit, in a single moving image file format.

6. The image playback apparatus according to claim 1, wherein the recording controller is configured to record the moving image data, the input information of the release signal, and the still image data generated by the still image generation unit, in separate files.

7. The image playback apparatus according to claim 1, wherein the display controller is configured to display, on the display device, a moving image selection screen for selecting moving image data as a playback target among a plurality of moving image data recorded on the recording device, and the moving image selection screen includes a representative image of each of the moving image data, the still image data associated with each of the moving image data, and the playback position information that indicates one of the first mark and the second mark, each of the first and second marks indicating the input timing of the release signal.

8. A non-transitory computer-readable recording medium recording an image playback program for causing an image playback apparatus for playing back, on a display device, moving image data as a playback target from among moving image data recorded on a recording device to execute:

generating playback-oriented moving image data from the moving image data as the playback target;

playing back, on the display device, the generated playback-oriented moving image data;

displaying, on the display device, playback position information that indicates a playback position of an image being played back on the display device among a bundle of the moving image data linearly arranged in time series;

displaying, on the playback position information, a first mark that indicates an input timing of the release signal input during playback of the moving image data, and a second mark that has a different display mode from the display mode of the first mark and that indicates an input timing of the release signal based on the input information recorded in association with the moving image data;

receiving input of a release signal during playback of the playback-oriented moving image data;

generating, from the moving image data, still image data that correspond to a playback image being played back on the display device at a time of input of the release signal;

recording, on the recording device, the generated still image data, in association with the moving image data; and when the release signal is input during recording of the moving image data, recording input information of a release signal in association with the moving image data.

* * * * *